US012649041B2

(12) United States Patent
Khalil

(10) Patent No.: US 12,649,041 B2
(45) Date of Patent: Jun. 9, 2026

(54) CONTINUOUS AUDITORY BRAIN STIMULATION

(71) Applicant: The Regents of the University of California, Oakland, CA (US)

(72) Inventor: Alexander Konrad Khalil, Ballyfeard (IE)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 1051 days.

(21) Appl. No.: 17/779,097

(22) PCT Filed: Nov. 24, 2020

(86) PCT No.: PCT/US2020/062104
§ 371 (c)(1),
(2) Date: May 23, 2022

(87) PCT Pub. No.: WO2021/108460
PCT Pub. Date: Jun. 3, 2021

(65) Prior Publication Data
US 2023/0001127 A1     Jan. 5, 2023

Related U.S. Application Data

(60) Provisional application No. 62/939,882, filed on Nov. 25, 2019.

(51) Int. Cl.
*A61M 21/00*     (2006.01)
*H04R 25/00*     (2006.01)

(52) U.S. Cl.
CPC ............. *A61M 21/00* (2013.01); *H04R 25/00* (2013.01); *A61M 2021/0027* (2013.01);
(Continued)

(58) Field of Classification Search
CPC .......................... A61M 21/00–02; A61B 5/38
See application file for complete search history.

(56) References Cited

U.S. PATENT DOCUMENTS 5,356,368 A     10/1994   Monroe
5,402,797 A      4/1995   Akiyama et al.
(Continued)

FOREIGN PATENT DOCUMENTS

CA         2822846       4/2015
CN       105323690       2/2016
(Continued)

OTHER PUBLICATIONS

"Chinese Application Serial No. 202080092321.2, Office Action mailed May 27, 2023", w English Translation, 15 pgs.
(Continued)

*Primary Examiner* — Thaddeus B Cox
(74) *Attorney, Agent, or Firm* — SCHWEGMAN LUNDBERG & WOESSNER, P.A.

(57)     ABSTRACT

Systems and methods discussed herein can be used to augment or induce brainwave behavior, such as using auditory stimulus, in an example, ambient acoustic information can be received, selectively modulated, and presented to a user in a substantially continuous manner. A low frequency portion of received ambient acoustic information can be modulated and then combined with a high frequency portion of the ambient acoustic information to produce a combined signal. The combined signal can be provided to the user as an auditory stimulation signal.

14 Claims, 8 Drawing Sheets

(52) U.S. Cl.

CPC .............. *A61M 2205/3375* (2013.01); *A61M 2205/505* (2013.01); *A61M 2210/0662* (2013.01); *A61M 2230/63* (2013.01); *H04R 2225/025* (2013.01)

(56) References Cited

U.S. PATENT DOCUMENTS

| | | | |
|---|---|---|---|
| 7,674,224 | B2 | 3/2010 | Hewett |
| 8,932,218 | B1 | 1/2015 | Thompson |
| 9,432,777 | B2 | 8/2016 | Lunner et al. |
| 9,563,273 | B2 | 2/2017 | Mann |
| 9,700,261 | B2 | 7/2017 | Lunner |
| 9,886,965 | B1 | 2/2018 | Ahmet et al. |
| 9,987,459 | B2 | 6/2018 | Donnet et al. |
| 10,440,487 | B2 | 10/2019 | Jensen et al. |
| 11,172,859 | B2 | 11/2021 | Connor |
| 2006/0258950 | A1 | 11/2006 | Esty et al. |
| 2011/0054241 | A1* | 3/2011 | Jensen .................... G10L 25/84 |
| | | | 600/28 |
| 2013/0131537 | A1 | 5/2013 | Tam |
| 2013/0216055 | A1 | 8/2013 | Wanca |
| 2013/0343584 | A1 | 12/2013 | Bennett |
| 2014/0369537 | A1 | 12/2014 | Pontoppidan et al. |
| 2015/0168996 | A1 | 6/2015 | Sharpe et al. |
| 2015/0283019 | A1 | 10/2015 | Feingold |
| 2016/0112022 | A1* | 4/2016 | Butts ........................ H04R 1/10 |
| | | | 381/100 |
| 2016/0235328 | A1 | 8/2016 | Elberling et al. |
| 2017/0180882 | A1 | 6/2017 | Lunner et al. |
| 2018/0055402 | A1 | 3/2018 | Izvarina |
| 2018/0236232 | A1 | 8/2018 | Soulet De Brugiere et al. |
| 2018/0317795 | A1 | 11/2018 | Couser |
| 2019/0255350 | A1 | 8/2019 | Malchano et al. |
| 2019/0269936 | A1 | 9/2019 | Malchano et al. |
| 2020/0252730 | A1* | 8/2020 | Frieding ................ A61B 5/121 |
| 2020/0265827 | A1* | 8/2020 | Hewett ................ A61M 21/02 |

FOREIGN PATENT DOCUMENTS

| | | |
|---|---|---|
| CN | 105877762 | 8/2016 |
| CN | 107921251 | 4/2018 |
| CN | 115038486 | 4/2024 |
| DE | 102011052186 | 1/2016 |
| EP | 4065204 | 5/2025 |
| JP | 2010520683 | 6/2010 |
| JP | 5317277 | 7/2013 |
| JP | 5756992 | 6/2015 |
| JP | 2023502788 | 1/2023 |
| JP | 7579857 | 10/2024 |
| KR | 20160117882 | 10/2016 |
| WO | WO-2013014210 A1 | 1/2013 |
| WO | 2017086353 | 5/2017 |
| WO | 2017094927 | 6/2017 |
| WO | 2018013835 | 1/2018 |
| WO | 2018030404 | 2/2018 |
| WO | 2018068050 | 4/2018 |
| WO | 2018110534 | 6/2018 |
| WO | 2018159519 | 9/2018 |
| WO | 2019060298 | 3/2019 |
| WO | 2019152136 | 8/2019 |

OTHER PUBLICATIONS

"Japanese Application Serial No. 2022-530311, Response filed Jun. 19, 2024 to Examiners Decision of Final Refusal mailed Feb. 20, 2024", w current English claims, 21 pgs.

"European Application Serial No. 20893220.2, Response filed Sep. 3, 2024 to Extended European Search Report mailed Mar. 7, 2024", 13 pgs.

"International Application Serial No. PCT US2020 062104, International Preliminary Report on Patentability mailed Jun. 9, 2022", 7 pgs.

"Japanese Application Serial No. 2022-530311, Notification of Reasons for Refusal mailed May 9, 2023", w English translation, 9 pgs.

"Chinese Application Serial No. 202080092321.2, Response Filed Sep. 20, 2023 to Office Action mailed May 27, 2023", W English Claims, 21 pgs.

"Japanese Application Serial No. 2022-530311, Response Filed Nov. 9, 2023 to Notification of Reasons for Refusal mailed May 9, 2023", W English Claims, 21 pgs.

"Japanese Application Serial No. 2022-530311, Examiners Decision of Final Refusal mailed Feb. 20, 2024", w English Translation, 9 pgs.

"European Application Serial No. 20893220.2, Extended European Search Report mailed Mar. 7, 2024", 9 pgs.

International Application Serial No. PCT/US2020/062104, International Search Report mailed Feb. 11, 2021, 2 pgs.

International Application Serial No. PCT/US2020/062104, Written Opinion mailed Feb. 11, 2021, 5 pgs.

* cited by examiner

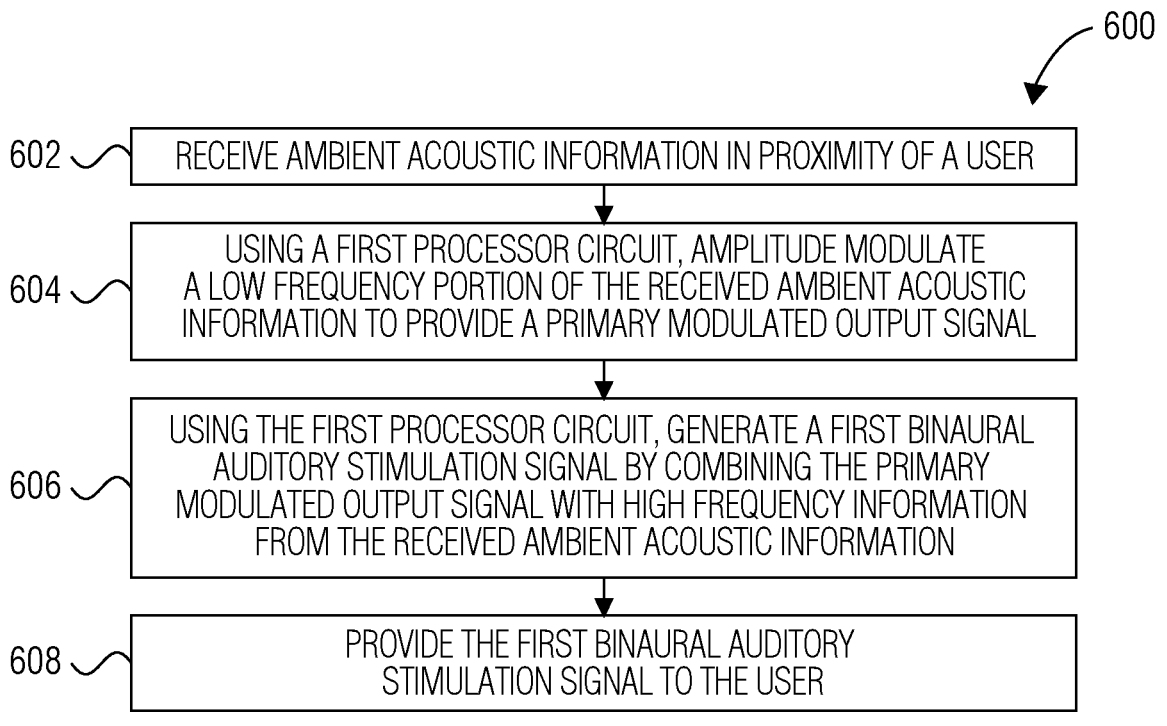

600

602  RECEIVE AMBIENT ACOUSTIC INFORMATION IN PROXIMITY OF A USER

604  USING A FIRST PROCESSOR CIRCUIT, AMPLITUDE MODULATE
A LOW FREQUENCY PORTION OF THE RECEIVED AMBIENT ACOUSTIC
INFORMATION TO PROVIDE A PRIMARY MODULATED OUTPUT SIGNAL

606  USING THE FIRST PROCESSOR CIRCUIT, GENERATE A FIRST BINAURAL
AUDITORY STIMULATION SIGNAL BY COMBINING THE PRIMARY
MODULATED OUTPUT SIGNAL WITH HIGH FREQUENCY INFORMATION
FROM THE RECEIVED AMBIENT ACOUSTIC INFORMATION

608  PROVIDE THE FIRST BINAURAL AUDITORY
STIMULATION SIGNAL TO THE USER

702 — RECEIVE AMBIENT
ACOUSTIC INFORMATION

704 — BELOW SPL
THRESHOLD?

NO

706

PROVIDE AUDITORY STIMULATION
SIGNAL BASED ON MODULATED
AMBIENT ACOUSTIC INFORMATION

YES

708 — PROVIDE AUDITORY STIMULATION
SIGNAL BASED ON NOISE SIGNAL

CONTINUOUS AUDITORY BRAIN STIMULATION

CROSS-REFERENCE TO RELATED APPLICATIONS

This patent application is a U.S. National Stage Filing under 35 U.S.C. 371 from International Application No. PCT/US2020/062104, filed on Nov. 24, 2020, and published as WO 2021/108460 A1 on Jun. 3, 2021, which claims the benefit of priority to U.S. Provisional Patent Application No. 62/939,882, filed on Nov. 25, 2019, each of which is incorporated by reference herein in its entirety.

BACKGROUND

The spectral composition of oscillating electric signals in the brain, often referred to as brainwaves, are the result of populations of neurons firing in synchrony, and are known to reflect different mental or cognitive states. For example, a neurotypical adult human brain will show relatively more activity in the Delta band (e.g., 0.5-4 Hz) during sleep but relatively more Beta band activity (e.g., 12-35 Hz) when alert and actively thinking. Further, certain disorders are associated with changes in spectral composition. For example, patients with Parkinson's disease exhibit more Delta activity when awake and lesser activity across all frequency bands than neurotypicals. In another example, differences in a ratio of Theta to Beta band activity can be associated with Attention Deficit Hyperactivity Disorder. Further, individuals suffering dementia of any kind show attenuated Theta band activity.

In some examples, brainwaves or electrical frequency activity in a brain can be modulated or changed in response to various stimuli presented to the eyes or ears, or using tactile stimuli. For example, repetitive stimuli presented to a user at a particular frequency can encourage the electrical activity of the user's brain to shift toward the same particular frequency. This phenomenon or changing the brainwave behavior of a user is referred to as entrainment.

Various examples of delivering continuous auditory stimulation for entrainment have been proposed to modulate brainwaves for therapeutic effect. The auditory stimulation can be presented to a user using headphones or earphones. In some examples, the auditory stimulation is provided by modulating various aspects of a recorded audio program, such as a music program.

One form of auditory stimulation includes "binaural beats." Binaural beats are an auditory illusion or brain response that is created by presenting different auditory information or source signals to respective ears of a listener. The different auditory information differs in frequency. The difference between the information presents itself to the listener as an amplitude-modulated signal resulting from the phase relationship of the source signals. The resulting "beats" can be perceived by the listener as an auditory beat and it can be used to entrain different rhythms or cortical potentials in the listener's brain.

BRIEF SUMMARY

The present inventor has recognized, among other things, that a problem to be solved includes providing auditory stimulation for entrainment without using noises that would be distracting or disruptive for a user. In an example, a solution to the problem can include using amplitude modulation of ambient sounds. In an example, the solution can include modulating existing sounds in a user's environment, for example, at selected frequencies that may not interfere with important functions like speech processing. In an example, frequencies presented to the user can be continuously modulated in a way that mimics normal, healthy brain function.

This Summary is intended to provide a brief overview of subject matter of the present application. It is not intended to provide an exclusive or exhaustive explanation of the invention or inventions discussed herein. The detailed description is included to provide further information about the present patent application.

BRIEF DESCRIPTION OF THE SEVERAL VIEWS OF THE DRAWINGS

To easily identify the discussion of any particular element or act, the most significant digit or digits in a reference number refer to the figure number in which that element is first introduced.

FIG. 6 illustrates generally an example of a first method that can be used to provide an auditory stimulation signal to a user.

DETAILED DESCRIPTION

Figure 1:
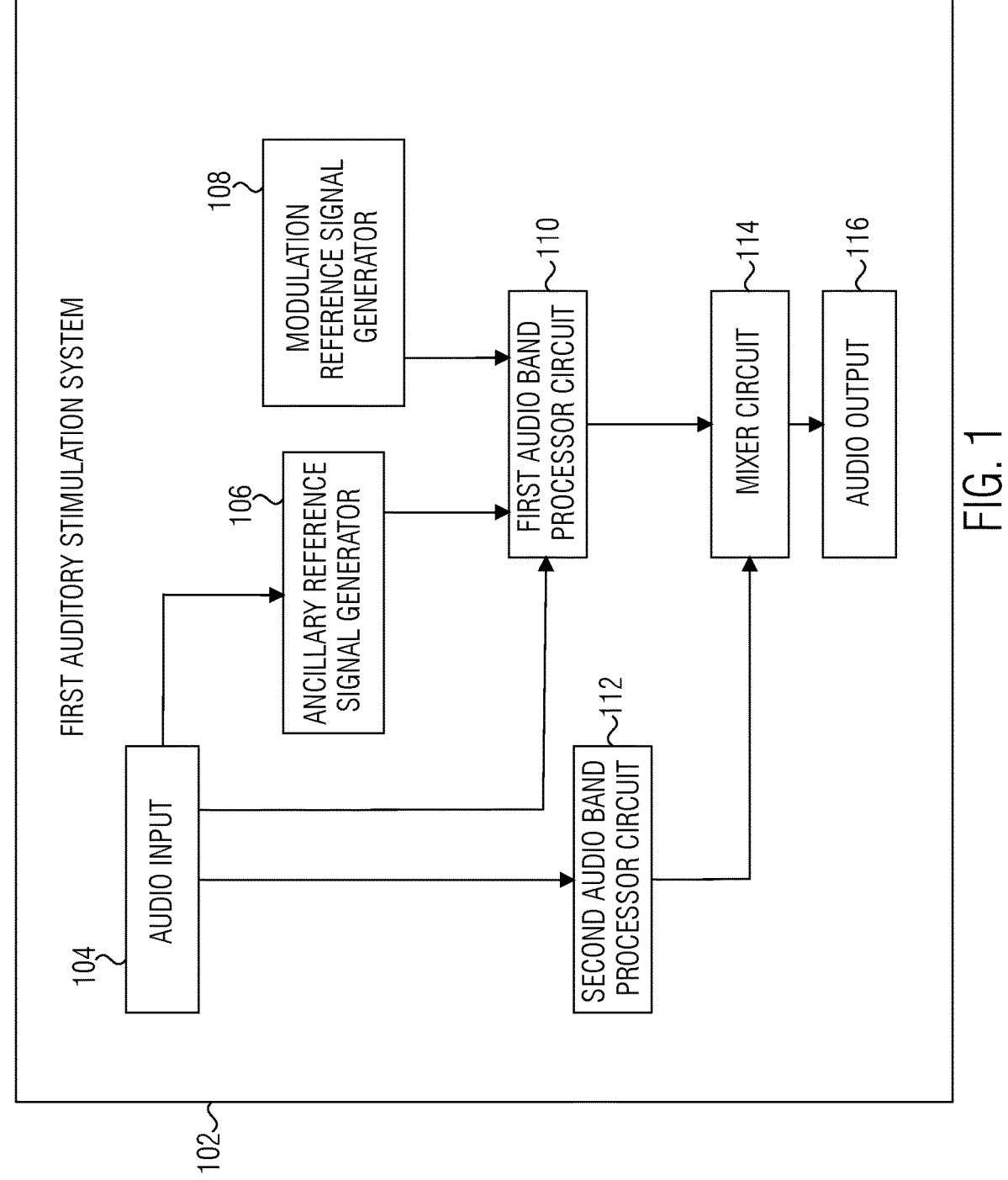
FIG. 1 illustrates generally an example of a first auditory stimulation system.

The description that follows describes systems, methods, techniques, instruction sequences, and computing machine program products that illustrate example embodiments of the present subject matter. In the following description, for purposes of explanation, numerous specific details are set forth in order to provide an understanding of various embodiments of the present subject matter. It will be evident, however, to those skilled in the art, that embodiments of the present subject matter may be practiced without some or other of these specific details. Examples merely typify possible variations. Unless explicitly stated otherwise, structures (e.g., structural components, such as modules) are optional and may be combined or subdivided, and operations (e.g., in a procedure, algorithm, or other function) may vary in sequence or be combined or subdivided.

Various systems and methods discussed herein facilitate solving a technical problem of inducing particular brain behavior, or entrainment, using sounds or information in a user's environment. As such, one or more of the systems and methods described herein may obviate a need for certain efforts or computing resources that otherwise would be involved in therapy signal generation, or processing or use of other signals that could be distracting or unpleasant for a user, such as signals unrelated to the user's environment, particularly over long periods of time. As a result, resources used by one or more machines, databases, or devices (e.g., within the environment) may be reduced. Examples of such computing resources include processor cycles, network traffic, memory usage, data storage capacity, power consumption, or network bandwidth.

Systems and methods discussed herein can be used to provide auditory stimulation without injecting distracting or disruptive noise into a user's environment. In an example, a solution to the problem can include using amplitude modulation of ambient sounds or other sounds existing in a user's environment. That is, ambient sounds or other acoustic information in the vicinity of the user can be used as a carrier signal for amplitude-modulated, therapeutic auditory stimulation signals. In an example, the amplitude modulation can be introduced at selected frequencies that may not interfere with important functions like speech processing. In some examples, amplitude-modulated signals can be presented to a user continuously, and can be modulated in a way that mimics normal, healthy brain function. The amplitude-modulated signals can be presented to a user as an auditory stimulation signal, such as using one or both ears, and can be used to induce particular brainwaves or brainwave behavior. The particular brainwave activity or frequency to be induced can depend upon the particular therapy or objective for delivering the stimulus.

The present inventor has further recognized that a problem to be solved includes providing a tailored or user-specific auditory stimulation solution. For example, solutions using loudspeakers may take a "one size fits all" approach, assuming that everyone in a given environment may benefit from stimulation by the same audio frequencies. The present inventor has recognized that a solution to the problem can include allowing each user to receive his or her optimal frequency or frequencies, even while in the same environment as other users. In an example, the solution can include using the same ambient sound or sounds as a carrier for a variety of waveforms such as for a variety of respective users.

The present solution can include or use continuous auditory stimulation that induces brainwaves to couple with, or "entrain" to, the frequency of presented stimuli. Such stimulation has been found to have an effect and significant potential therapeutic value in a variety of use cases, including for alertness, or for treatment of diseases or disorders such as dementias, age-related memory loss, Parkinson's Disease, sleep disorders, speech issues like stuttering, depression, or anxiety, among others, in which certain brainwave rhythms are attenuated when compared with those of "normal" or neurotypical brains. The present solution allows for substantially continuous brain stimulation over long periods without distracting or disrupting the user.

In an example, the present solution includes amplitude modulation of ambient sound for continuous brain stimulation, for example, without using generated or recorded sounds to intrude on the user's senses, such as would otherwise mask a user's experience of the world and isolate or endanger the user. Rather, the present solution can include or use ambient sound in a user's environment as a carrier for an auditory stimulation signal.

In an example, the present solution can include or use frequency-selective amplitude modulation. Some frequency bands can be relatively more important for speech or other signal comprehension. Amplitude modulating frequencies in such bands can degrade speech (or other signal) comprehension and thus detract from a user's quality of life and/or can limit deployment of a potentially beneficial therapy. This problem is addressed using filtering such as to select only particular frequencies or frequency bands for modulation. In some examples, some relatively important frequencies can be unprocessed or unmodulated. In an example, the present systems and methods can be further used to augment hearing at these or other particular frequencies or frequency bands using spectral equalization, such as similarly to the way that a hearing aid can selectively tune various frequencies or bands to enhance intelligibility of particular signals. In an example, the systems and methods discussed herein can be integrated with, or used to augment various functions of, hearing aids, and can be tailored to a particular user's audiogram.

In an example, the present invention can include modulating select frequency bands, such as bands below or above one or more frequency thresholds. For example, unmodulated acoustic information can correspond to human speech-related frequencies. Acoustic information above or below the speech range can be modulated, such as without detrimental effect to the user's experience or understanding of speech. Many of the examples discussed herein refer to modulation of low frequency information e.g., 200 Hz or less), however, modulation can similarly be applied to higher frequency information above the speech range, such as at frequencies above about 8 kHz.

In an example, the systems and methods discussed herein can be used to provide therapy in the form of "binaural beats." Binaural beats are provided by presenting respective signals of slightly different frequencies to each of a listener's ears. The signals can cause the user's brainstem to produce an oscillation at a frequency that represents the difference between the two stimulation signal frequencies. For example, ambient sound can be amplitude modulated at, e.g., 400 Hz in the right ear and 406 Hz in the left ear, causing the brainstem to produce an oscillation at 6 Hz, which can be measured across the entire scalp. Binaural beats can thus be used to modulate an ambient signal for continuous auditory stimulation.

In an example, the present solution can include using added sound when ambient sound pressure levels drop below a specified threshold level that may be needed to carry stimulation frequency(ies). For example, a noise signal (e.g., white noise, pink noise, brown noise, or other noise signal) can be generated and used as a carrier signal. In an example, the noise signal can be amplitude modulated to a desired frequency when ambient sound pressure levels in a user's environment drop below the specified threshold level that may be used or needed to otherwise carry a modulation signal, in an example, the noise signal can pass through a low pass filter along with, or can be processed separately from, the rest of the amplitude modulated signal, such as according to a user-defined filter cutoff. Using this noise-insertion or noise-bridging technique, stimulation frequencies can be presented to a user without disruption of the user's daily activities, such as throughout the entirety of the user's waking hours, allowing for an unprecedented amount of stimulation. In other words, acoustic information from a user's environment can be used for auditory stimulation when the acoustic information meets or exceeds a specified minimum threshold sound pressure level and a modulated noise signal can be used to occupy or bridge periods of time when the acoustic information does not meet the specified minimum threshold level.

In an example, the noise technique can be beneficial to users who suffer from tinnitus. There are many people who suffer severe tinnitus from exposure to loud sounds (e.g., veterans) and who would benefit from auditory stimulation that is evenly maintained between loud and quiet environments (those with tinnitus experience the most discomfort in quiet areas). In an example, an auditory stimulation signal to treat tinnitus can be provided at or around 10 Hz. For example, amplitude modulation of a 10 kHz masking noise can be provided to treat tinnitus by changing brain rhythms, Other signals can similarly be used. In an example, filtering techniques, such as can be helpful to treat various types of tinnitus, can be applied to ambient acoustic information or to a noise signal for use in auditory stimulation. A particular filtering technique can include providing a notch-filtered and amplitude-modulated auditory stimulation signal where the notch is centered at or near a frequency corresponding to a user's particular tonal tinnitus.

In an example, the present solution can include or use stimuli that are selected or designed to resemble neurotypical brainwave patterns. Some prior techniques for auditory brain stimulation make use of highly regular, sinusoidal waveforms. These waveforms, while convenient to generate and easy to find in spectrographic imagery, may not reflect the brainwaves of healthy, neurotypical individuals. Furthermore, exposure to highly symmetrical and fixed-frequency waves over long periods could be problematic for some users. In addition, the brain tends to habituate (or become increasingly less sensitive) to perfectly regular stimuli and therefore, over time, stimulation with a sinusoidal wave of unchanging amplitude can have a decreasing effect, such as leading to diminished effects of auditory stimulation. Typical brainwaves in humans can be described as "bursty," meaning they happen in bursts of activity, frequently changing in amplitude, and quickly starting and stopping. Such typical brainwaves can also drift slightly in frequency throughout different bursts.

In an example, systems and methods presented herein can addresses these problems and others, such as by mimicking various behaviors or features of neurotypical brainwaves. These features can be described in terms of spectrographic behavior, signal morphology, "burstiness," or "drift" of typical or target brainwave activity. Burstiness can refer to brainwaves that are not continuous but tend to take place in bursts. Drift can refer to brainwaves that do not remain rigidly at a fixed frequency but instead drift somewhat throughout a burst or over the course of multiple bursts. In an example, the solution herein can include or use such naturalistic frequencies by recording brainwave patterns from neurotypical brains and using those recorded waveforms or features thereof as references for amplitude modulation of other signals, including ambient acoustic signals, for delivery to a user.

FIG. 1 illustrates generally an example of a first auditory stimulation system 102. The first auditory stimulation system 102 includes various components that can be used to prepare or generate an auditory stimulation signal, such as can be used to induce or augment brainwave activity in a user. As used herein, various signals are referred to in the singular form, however, plural signals can similarly or equivalently be used. For example, references to a particular signal or signal type can be understood to encompass one or multiple signals, such as can be provided using corresponding one or multiple channels (e.g., using stereo channels).

The example of the first auditory stimulation system 102 includes a First audio input 104, an ancillary reference signal generator 106, a modulation reference signal generator 108, a first audio band processor circuit 110, a second audio processor circuit 112, a mixer circuit 114, and an audio output 116. In an example, the First audio input 104 can include any input that is configured to sense or receive ambient or other signal information in the vicinity of the user. In an example, the First audio input 104 comprises a single-channel microphone and is configured to provide a monophonic microphone signal. In other examples, the First audio input 104 can include a multiple-channel audio input device, such as a stereo microphone, configured to provide two or more microphone signals.

The first auditory stimulation system 102 can include the modulation reference signal generator 108. The modulation reference signal generator 108 can be configured to generate or provide a modulation reference signal for use in modulation of one or more other signals. For example, the modulation reference signal generator 108 can be configured to generate a sinusoidal reference signal, such as can be used in combination with another signal, such as a carrier signal, to provide an amplitude modulated signal. In an example that includes amplitude modulation, the modulation reference signal generator 108 can generate a message signal that can be combined with, or used as a reference to modulate, a carrier signal. In an example, the carrier signal can comprise ambient information from the First audio input 104, a noise signal, or other signal.

The first audio band processor circuit 110 can comprise an audio signal processor that is configured to receive information or a signal from the First audio input 104 and to receive information or a signal from the modulation reference signal generator 108. For example, the first audio band processor circuit 110 can receive an ambient audio signal from the First audio input 104 and a sinusoidal reference signal from the modulation reference signal generator 108. The first audio band processor circuit 110 can further include equalization, gain adjustment, or other filtering or processing circuitry.

In an example, the first audio band processor circuit 110 is configured to receive the ambient audio signal from the First audio input 104 and process the received signal with a low-pass filter to provide a low-passed intermediate signal. The low-passed intermediate signal can be further processed by the first audio band processor circuit 110, such as according to a reference signal received from the modulation reference signal generator 108, to provide a modulated signal. That is, the first audio band processor circuit 110 can be configured to provide a modulated signal that is an amplitude-modulated version of the low-frequency information in the acoustic information from the First audio input 104, and characteristics of the amplitude modulation can be defined at least in part by information from the modulation reference signal generator 108. The first audio band processor circuit 110 can provide the modulated signal to the mixer circuit 114. In an example, the modulated signal can include two or more channels of information, such as corresponding to left and right channels of a stereo pair. The information in the respective channels can be similarly or differently modulated, such as based on the same modulation reference signal from the modulation reference signal generator 108.

In an example, the second audio band processor circuit 112 can comprise an audio processor that is configured to receive information or a signal from the First audio input 104. The second audio band processor circuit 112 can process the received signal with a high-pass filter to provide a high-passed intermediate signal. The high-passed interme-diate signal can be further processed by the second audio band processor circuit 112, such as according to various gain, equalization, or other filter parameters. For example, the second audio band processor circuit 112 can include a speech intelligibility augmentation filter that is configured to amplify components or signal bands of the high-passed intermediate signal, or of the signal as received from the First audio input 104, that are associated with human speech intelligibility. For example, the augmentation filter can be configured to boost information in a frequency band of about 750 Hz to 2.5 kHz. In an example, the augmentation filter can be configured to boost sibilance, for example, in a frequency band of about 2-10 kHz. Other filters can simi-larly be used. In the example of FIG. 1, the second audio band processor circuit 112 can provide an adjusted ambience signal to the mixer circuit 114. In an example, the adjusted ambience signal can include two or more channels of information, such as corresponding to left and right channels of a stereo pair.

The mixer circuit 114 can be configured to combine or mix the modulated signal from the first audio band processor circuit 110 and the adjusted ambience signal from the second audio band processor circuit 112 and provide an auditory stimulation signal to the audio output 116. The mixer circuit 114 or the audio output 116 can include other gain, filtering, or other processing circuitry to further adjust the auditory stimulation signal. In an example, the mixer circuit 114 is a multiple-channel mixer that is configured to combine infor-mation from multiple different channels simultaneously. In an example, the mixer circuit 114 is configured to receive the modulated signal from the modulation reference signal generator 108 as a single-channel signal to be mixed with different left and right channels of the adjusted ambience signal from the second audio band processor circuit 112.

The audio output 116 can include an interface configured to provide the auditory stimulation signal, or a further processed version thereof, to the user. In an example, the audio output 116 includes a headphone interface configured to provide the auditory stimulation signal to one or both ears of the user using headphones, earphones, bone-conduction devices, hearing aids, or other sources.

The example of FIG. 1 includes the ancillary reference signal generator 106. In an example, the ancillary reference signal generator 106 includes a noise generator that can be selectively used to generate a noise signal. The noise signal can comprise one or multiple different types of noise signals, such as white noise, pink noise, brown noise, or other type of noise signal, or a combination of different types of noise signals. In an example, the ancillary reference signal gen-erator 106 can be configured to generate the noise signal when an ambient sound pressure level (SPL) (e.g., an average or RMS sound pressure level) of an environment is less than a specified minimum sound pressure threshold amount. In an example, the ambient SPL can be determined by the first auditory stimulation system 102 using informa-tion from the First audio input 104 or from another source, such as from a separate SPL meter or sensor.

The ancillary reference signal generator 106 can provide the noise signal to the first audio band processor circuit 110. In an example, the first audio band processor circuit 110 can prepare the modulated signal using the noise signal and a modulation reference signal. In an example, the first audio band processor circuit 110 can prepare the modulated signal using the noise signal and using the low-passed intermediate signal that is based on information from the First audio input 104.

Figure 2:
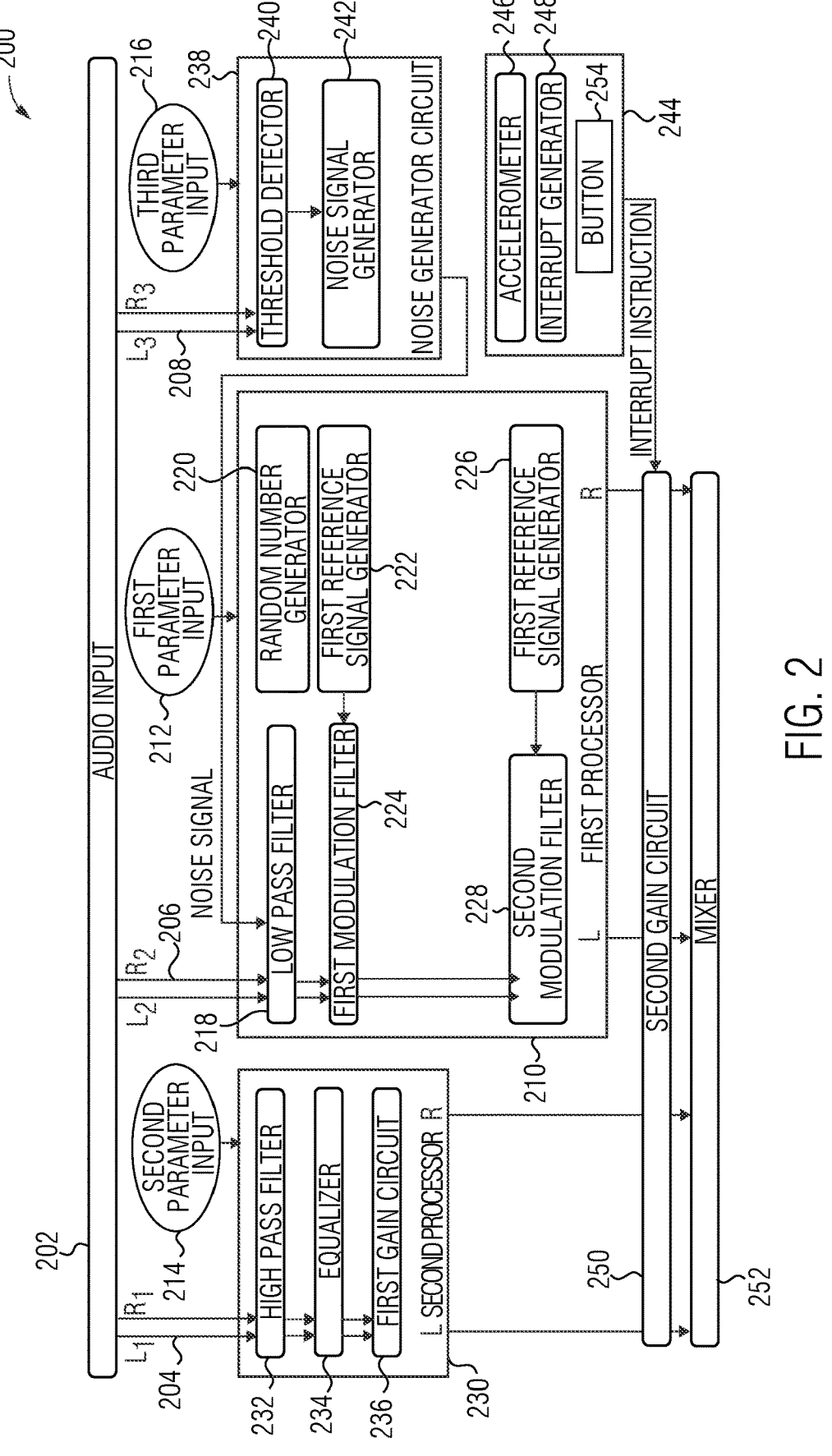
FIG. 2 illustrates generally an example of a second auditory stimulation system.

FIG. 2 illustrates generally an example of a second auditory stimulation system 200. The second auditory stimu-lation system 200 can include various modules or compo-nents that are the same or similar to those discussed above in the example of FIG. 1. The example of FIG. 2 is provided to further illustrate various features or components of some modules or components in a system for augmenting or inducing brainwave activity using auditory stimulation. In an example, one or more of the components of the second auditory stimulation system 200 can be implemented using a mobile device, such as a mobile telephone, tablet com-puter, or other purpose-built device. The second auditory stimulation system 200 can include or comprise one or more interfaces for receiving instructions that define an auditory stimulation program. The interfaces can be local or remote. For example, the second auditory stimulation system 200 can include a remote interface to receive instructions from a clinician or caregiver, and the second auditory stimulation system 200 can include a local interface to receive instruc-tions from a user.

The example of FIG. 2 includes a second audio input 202 such as can include a microphone or other acoustic sensor or audio signal receiver configured to provide one or more signals indicative of an acoustic environment of the user. The signals from the second audio input 202 can include a first audio input signal pair 204, a second audio input signal pair 206, and a third audio input signal pair 208, such as comprising stereo pairs of audio signals that include speech information, background noise, or other acoustic informa-tion from the environment of the user. In an example, the second audio input 202 can include or correspond to the first audio input 104 from the example of FIG. 1. In an example, the second audio input 202 comprises a receiver for broad-casted (e.g., via television or radio) signals or other acoustic signals.

The example of the second auditory stimulation system 200 includes a first processor circuit 210 and a second processor circuit 230. The first processor circuit 210 can include or correspond to the first audio band processor circuit 110 and the second processor circuit 230 can include or correspond to the second audio band processor circuit 112 from the example of FIG. 1. In some examples, the proces-sor circuits, among other circuits or functional blocks, can comprise different portions of the same processor circuit. In an example, the first processor circuit 210 is configured to receive the second audio input signal pair 206, and a noise signal, and provide a modulated signal that is based on one or both of the second audio input signal pair 206 and the noise signal. In an example, the first processor circuit 210 is configured to receive modulation parameters or instructions from a first parameter input 212. The parameters can include, for example, a modulation frequency, modulation depth, therapy duration, volume, or other parameters that can influence one or more characteristics of the modulated signal.

The first processor circuit 210 can include a low-pass filter 218. The low-pass filter 218 can receive the second audio input signal pair 206 and provide a low-passed signal that includes or represents a low frequency portion of the information in the second audio input signal pair 206. In an example, the low-pass filter 218 can receive the noise signal and provide a low-passed signal that includes or represents low frequency information from the noise signal.

The first processor circuit 210 can further include a first reference signal generator 222 and a first modulation filter 224. In an example, the first reference signal generator 222 can include or correspond to the modulation reference signal generator 108 from the example of FIG. 1. The first reference signal generator 222 can be configured to generate a first modulation signal, or a first information signal for an auditory stimulation signal. Parameters of the first modulation signal can be based on the first parameter input 212. In an example, the first modulation filter 224 can be configured to use the low-passed signal from the low-pass filter 218, such as comprising acoustic information from the second audio input 202 or the noise signal or both, together with the first modulation signal from the first reference signal generator 222 to provide a first modulated signal.

In an example, the first reference signal generator 222 can be configured to generate a sinusoidal signal at a frequency that depends, at least in part, on the first parameter input 212. In an example, the first reference signal generator 222 can be configured to generate a reference signal configured to drive Theta band activity, such as around 6 Hz, such as can be used to treat dementia-related memory loss. In an example, the first reference signal generator 222 can be configured to generate a reference signal configured to drive Gamma band activity, such as around 40 Hz, Gamma band activity can be used to augment or affect larger-scale brain activity such as related to memory, attention, or to treat disorders such as epilepsy or anxiety. In an example, the first parameter input 212 can be based on user-specific information about the user's disorder or disease state. For example, the first parameter input 212, such as received from a clinician, can be based on a specific target frequency that may be identified as being deficient in a particular patient or user.

The example of the first processor circuit 210 includes a second reference signal generator 226 and a second modulation filter 228. The second reference signal generator 226 can be configured to generate a second modulation signal for use in the auditory stimulation signal. Parameters of the second modulation signal can be based on the first parameter input 212. The second modulation signal can be different from the first modulation signal, such as in terms of frequency or amplitude or other characteristic. The second modulation filter 228 can be configured to use the first modulated signal from the first modulation filter 224 together with the second modulation signal from the second reference signal generator 226 to provide a second modulated signal. Additional instances of modulation reference signal generators and filters can similarly be used. In an example, the second reference signal generator 226 is configured to provide a second modulation signal that is substantially lower in frequency than the first modulation signal provided by the first reference signal generator 222. In an example, the second modulation filter 228 can apply the second modulation signal to create a bursty output signal that is configured to mimic neurotypical brainwave activity.

In an example, the first processor circuit 210 includes a random number generator 220 or other circuit or device that can be used to change spectrographic, morphologic, burst, or drift behavior of modulation provided by the second auditory stimulation system 200. For example, the first processor circuit 210 can be configured to use information from the random number generator 220 to apply a modulation algorithm that stochastically moves a center frequency of a target modulation frequency band about a user-defined bandwidth. For example, a Theta band comprises 4-8 Hz signals, so 4 Hz and 8 Hz can be set as outer bounds for movement or modulation of the signal. The algorithm can be configured to "move" the resulting signal modulation at various increments, such as 0.1 Hz. The resulting signal can then exhibit frequency drift similar to that of a natural Theta rhythm. In an example, a width of frequency drift or a rate of frequency drift can be adjusted or toggled on/off, such as according to a user input (e.g., using the first parameter input 212).

In an example, information from the random number generator 220 can be used to control overall amplitude or frequency characteristics of an amplitude-modulated signal provided by the first modulation filter 224, such as to provide a bursty or drifty signal that can be more immune to habituation. In an example, the random number generator 220 includes a quasi-random number generator, or pseudo-random number generator, that is configured to move in small increments. Small increments are generally preferred to help avoid drastic changes that could materialize as audible clicks or pops. In an example, the random number generator 220 is configured to provide a differently valued random output signal periodically, such as every 200 ms. The random output signal can be multiplied by a user-specified frequency (e.g., 0.5 Hz) to provide an amplitude control signal. The amplitude control signal can then be used, such as by the first modulation filter 224 or the second modulation filter 228, to slowly change an amplitude characteristic of the auditory stimulation signal to thereby help avoid user habituation to the stimulation signal.

In an example, the second auditory stimulation system 200 includes a second processor circuit 230. The second processor circuit 230 can include, among other things, a high-pass filter 232, an equalizer 234, and a first gain circuit 236. In an example, the second processor circuit 230 is configured to provide a high-passed signal, based on the first audio input signal pair 204, using the high-pass filter 232. The high-passed signal can be equalized using the equalizer 234 or gain-adjusted using the first gain circuit 236 and then outputted as a high frequency signal. The high frequency signal can represent relatively higher frequency information in the first audio input signal pair 204 received from the second audio input 202. For example, the high frequency signal can include speech information.

In an example, the second processor circuit 230 is configured to receive instructions or parameters from a second parameter input 214, The parameters can include, for example, a cutoff frequency for the high-pass filter 232, equalization parameters for the equalizer 234, or gain instructions for the first gain circuit 236. The parameters can influence various characteristics of the high frequency signal provided by the second processor circuit 230. In an example, the equalization parameters include information about a user's audiogram and can be used to configure the equalizer 234 to provide an adjusted signal that can help augment hearing or intelligibility for the user.

The example of FIG. 2 includes a noise generator circuit 238. The noise generator circuit 238 can include a threshold detector 240 that is configured to receive the third audio input signal pair 208. The threshold detector 240, such as can comprise a sound pressure level meter, can analyze the third audio input signal pair 208 to determine whether a specified sound pressure level threshold is met or exceeded by acoustic information in the environment of the second audio input 202. That is, the threshold detector 240 can determine whether there is sufficient acoustic information in the environment such that it can be modulated to deliver auditory stimulation to the user. If the threshold detector 240 determines that there is an insufficient amount of acoustic information, or that a sound pressure level threshold is not met, then a noise signal generator 242 can be activated to provide the noise signal to the first processor circuit 210. The first processor circuit 210 can modulate the noise signal to provide an auditory stimulation signal to the user, as described above.

In an example, the noise generator circuit 238 is configured to receive instructions or parameters from a third parameter input 216. The parameters can include, for example, a sound pressure level threshold at which to activate the noise signal generator 242, or a type of noise to be generated by the noise signal generator 242, among other things. In an example, the third parameter input 216 can include a sensitivity or hysteresis control for the threshold detector 240 or for the noise signal generator 242.

The example of FIG. 2 includes an interrupt circuit 244. The interrupt circuit 244 can produce an interrupt instruction that can interrupt one or more functions or features of the second auditory stimulation system 200. For example, the interrupt circuit 244 can include an accelerometer 246. The accelerometer 246 can be configured to sense an orientation or configuration of a device that includes the second audio input 202. When the accelerometer 246 is oriented in a specified manner, for example upright or in another predefined orientation, then an interrupt generator 248 can be caused to generate the interrupt instruction. In an example, the interrupt circuit 244 can include a user input such as a button 254. When the button is pressed or actuated, the interrupt circuit 244 can generate the interrupt instruction. In an example, the interrupt instruction comprises a binary logic signal.

In an example, a second gain circuit 250 can receive the interrupt instruction from the interrupt circuit 244, the second modulated signal from the first processor circuit 210 and the high frequency signal from the second processor circuit 230. The second gain circuit 250 can be configured to provide gain-adjusted versions of the second modulated signal and the high frequency signal to a mixer circuit 252, and the mixer circuit 252 can be configured to provide an auditory stimulation output signal for the user. When the interrupt instruction is received from the interrupt circuit 244, the second gain circuit 250 can adjust a magnitude relationship between the second modulated signal and the high frequency signal. In an example, when the interrupt is asserted, the second auditory stimulation system 200 can deprioritize or mute the second modulated signal and provide the high frequency signal to the mixer circuit 252. In other examples, when the interrupt is asserted, the second auditory stimulation system 200 can deactivate such that no signals are permitted to pass to the mixer circuit 252. In other examples, when the interrupt is asserted, a different gain-adjusted version or amplified version of the input signal—such as without modulation—can be passed to the mixer circuit 252.

Figure 3:
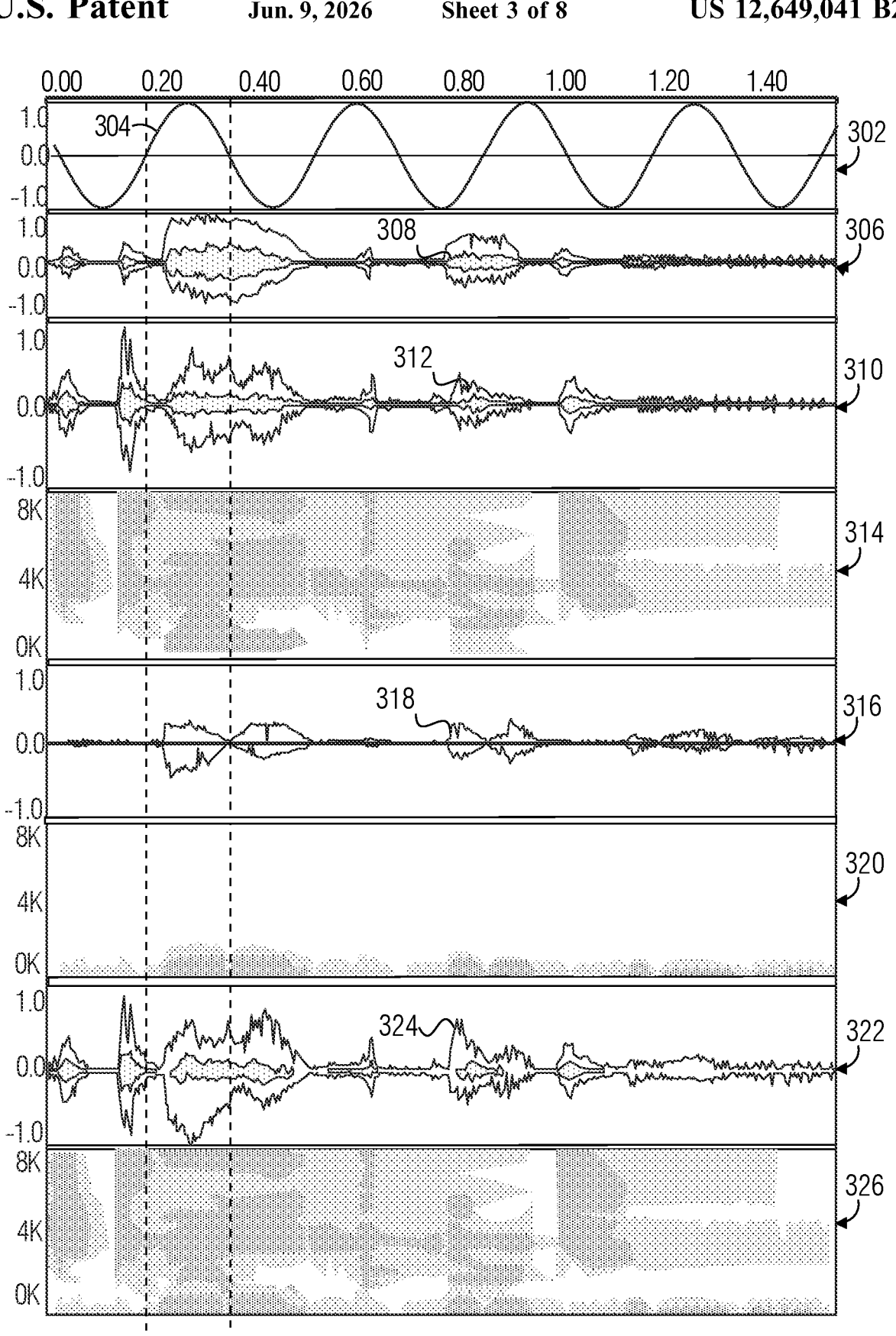
FIG. 3 illustrates generally several charts that illustrate time-aligned examples of various audio signals.

FIG. 3 illustrates generally several charts that illustrate time-aligned examples of various audio signals. For example, FIG. 3 includes a modulation signal reference chart 302, a first input signal chart 306, a high-passed signal chart 310, a first spectrogram 314, a low-passed and modulated signal chart 316, a second spectrogram 320, a first output signal chart 322, and a first output signal spectrogram 326. Along the x axis, the several charts have a common time axis and common scale. The y axis of the signal charts indicates relative amplitude, and the v axis of the spectrogram charts represent frequency (e.g., from about 0 Hz to about 8 kHz).

The example of the modulation signal reference chart 302 includes a reference signal waveform 304. The reference signal waveform 304 in FIG. 3 represents a 3 Hz sinusoidal wave. The reference signal waveform 304 can be used as a modulation reference or trigger to generate various other audio signals for auditory stimulation. In an example, the reference signal waveform 304 can represent an information signal or message signal that can be used together with a carrier signal to provide an amplitude-modulated auditory stimulation signal. Other reference signals, such as having different frequency or amplitude characteristics, can similarly be used.

The example of the first input signal chart 306 includes an input signal waveform 308. The input signal waveform 308 represents a speech signal. The speech signal can be unfiltered, and unmodulated. In an example, the input signal waveform 308 can represent an acoustic signal received by an audio input, such as the first audio input 104 or the second audio input 202. In an example, the input signal waveform 308 can represent a carrier signal to be modulated, such as according to a reference signal such as in the reference signal waveform 304.

The example of the high-passed signal chart 310 includes a high-passed signal waveform 312. The high-passed signal waveform 312 can represent a high-passed and gain-adjusted version of the input signal waveform 308. In an example, the high-passed signal waveform 312 can represent a signal generated by the second processor circuit 230 based on an acoustic signal from the second audio input 202.

The example of the first spectrogram 314 includes spectrogram information corresponding to the high-passed signal waveform 312. That is, the first spectrogram 314 represents a relative magnitude of various frequencies in the high-passed signal waveform 312. In the example of the first spectrogram 314, it can be observed that the high-passed signal waveform 312 includes information primarily at or above 1 kHz.

The example of the low-passed and modulated signal chart 316 includes a low-passed and modulated signal waveform 318. The low-passed and modulated signal waveform 318 can represent a low-passed and amplitude-modulated version of the input signal waveform 308. In the example, the low-passed and modulated signal waveform 318 thus represents an amplitude-modulated version of the lower-frequency information from the input signal waveform 308, and is amplitude modulated at 6 Hz, owing to the 3 Hz frequency of the reference signal waveform 304. The amplitude modulation processing doubles the frequency of the reference signal because the envelope of the resulting signal can be adjusted per-peak of the reference signal, that is, regardless of whether the peak is negative or positive. In an example, the low-passed and modulated signal waveform 318 can represent a signal generated by the first processor circuit 210 based on an acoustic signal from the second audio input 202.

The example of the second spectrogram 320 includes spectrogram information corresponding to the low-passed and modulated signal waveform 318. That is, the second spectrogram 320 represents a relative magnitude of various frequencies in the low-passed and modulated signal waveform 318. In the example of the second spectrogram 320, it can be observed that the low-passed and modulated signal waveform 318 includes information primarily at or below about 1 kHz. Furthermore, the amplitude modulation can be observed as whitespaces at intervals corresponding to the 6 Hz modulation signal. That is, the periodic attenuation of the amplitude of the low frequency information can be observed particularly at zero-crossings of the reference signal waveform 304, as indicated by the vertical dashed lines in the figure. The vertical dashed lines are provided to help illustrate the correspondence between the time-amplitude characteristics of zero-crossings and the reference signal waveform 304 and the several other signals and spectrograms.

The example of the first output signal chart 322 includes a first output signal waveform 324. The first output signal waveform 324 can represent a combination of the high-passed signal shown in the high-passed signal waveform 312 and the low-passed signal shown in the low-passed and modulated signal waveform 318. In an example, the output signal corresponding to the first output signal waveform 324 can be provided by the mixer circuit 252. In the example of the first output signal waveform 324, high frequency information, such as corresponding to speech intelligibility, can be maintained across the dips in low frequency information caused by the amplitude modulation. The first output signal spectrogram 326 illustrates generally the periodic nature of the amplitude of the low frequency information relative to the higher frequency information of the first output signal waveform 324. The first output signal waveform 324 can include one or more auditory stimulation signals that can be provided to a user.

Figure 4:
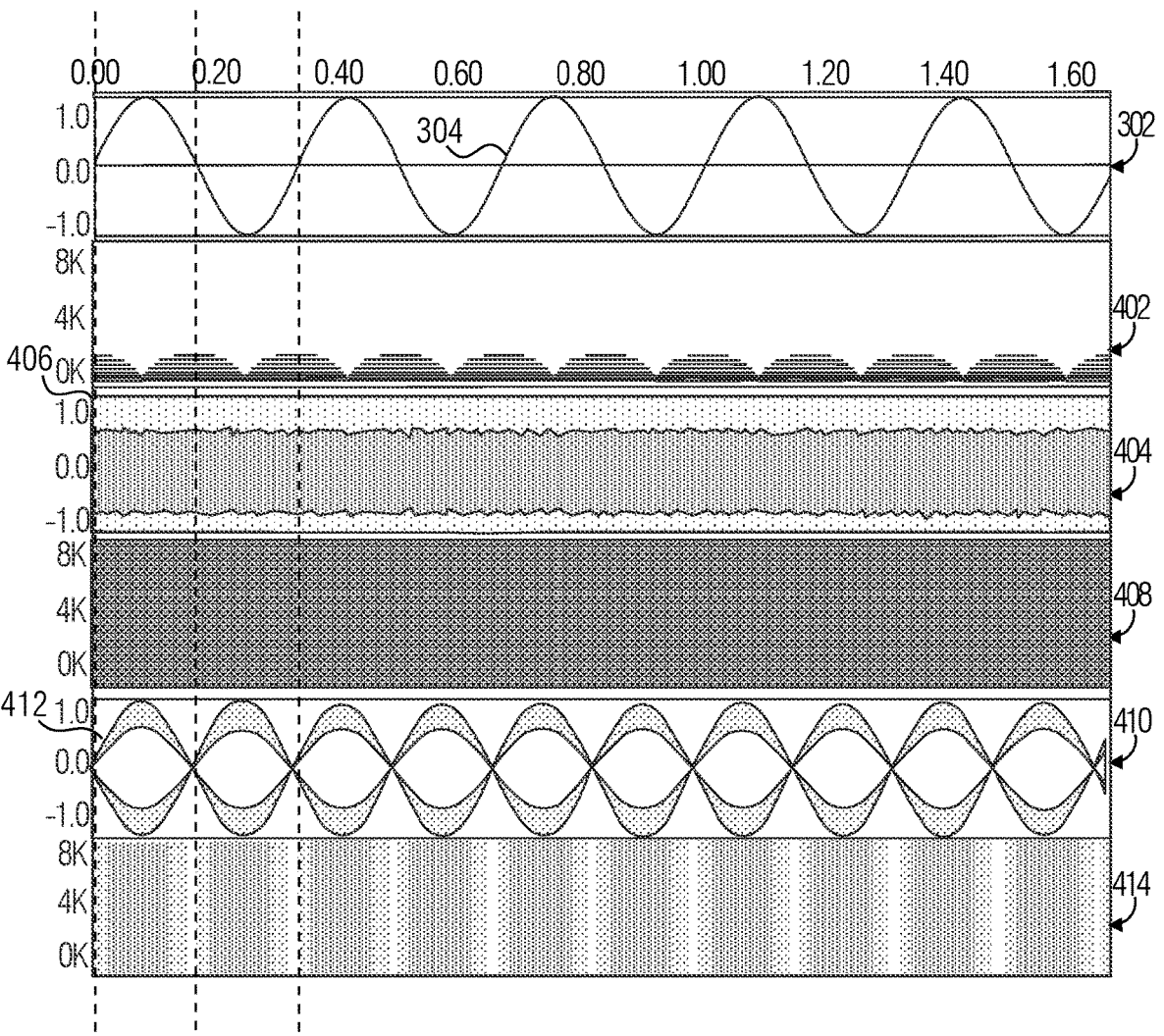
FIG. 4 illustrates generally several charts that illustrate time-aligned examples of various audio signals.

FIG. 4 illustrates generally several charts that illustrate time-aligned examples of various audio signals. For example, FIG. 4 includes a reference signal spectrogram 402, a noise signal chart 404, a noise signal spectrogram 408, a second output signal chart 410, and a second output signal spectrogram 414. Along the x axis, the several charts have a common time axis and common scale. The y axis of the signal charts indicates relative amplitude, and the y axis of the spectrogram charts represent frequency (e.g., from about 0 Hz to about 8 kHz). In the example of FIG. 4, the same modulation signal reference chart 302 and reference signal waveform 304 from the example of FIG. 3 can be used in amplitude modulation of a carrier signal, such as a noise signal.

The reference signal spectrogram 402 includes spectrogram information corresponding to low frequency components of the reference signal waveform 304. That is, the reference signal spectrogram 402 illustrates generally the relative magnitude of various frequencies in the reference signal waveform 304.

The noise signal chart 404 includes a noise signal waveform 406, such as representative of a white noise signal. In an example, the noise signal waveform 406 can represent a noise signal generated by the noise generator circuit 238. The noise signal spectrogram 408 shows a spectrogram corresponding to the noise signal waveform 406 and it indicates generally that the white noise signal includes approximately equal amplitude, on average, across the illustrated frequency band.

The second output signal chart 410 includes a second output signal waveform 412. The second output signal waveform 412 can represent an amplitude-modulated version of the noise signal corresponding to the noise signal waveform 406. The second output signal spectrogram 414 corresponds generally to the second output signal waveform 412 and illustrates the periodicity of modulated signal, at 6 Hz, due to the reference signal waveform 304. That is, the examples of the second output signal chart 410 and the second output signal spectrogram 414 illustrate an amplitude-modulated white noise signal, as-modulated according to the reference signal waveform 304. In an example, the amplitude-modulated white noise signal can be provided by the first processor circuit 210 as one or more auditory stimulation signals.

Figures 5A, 5B:
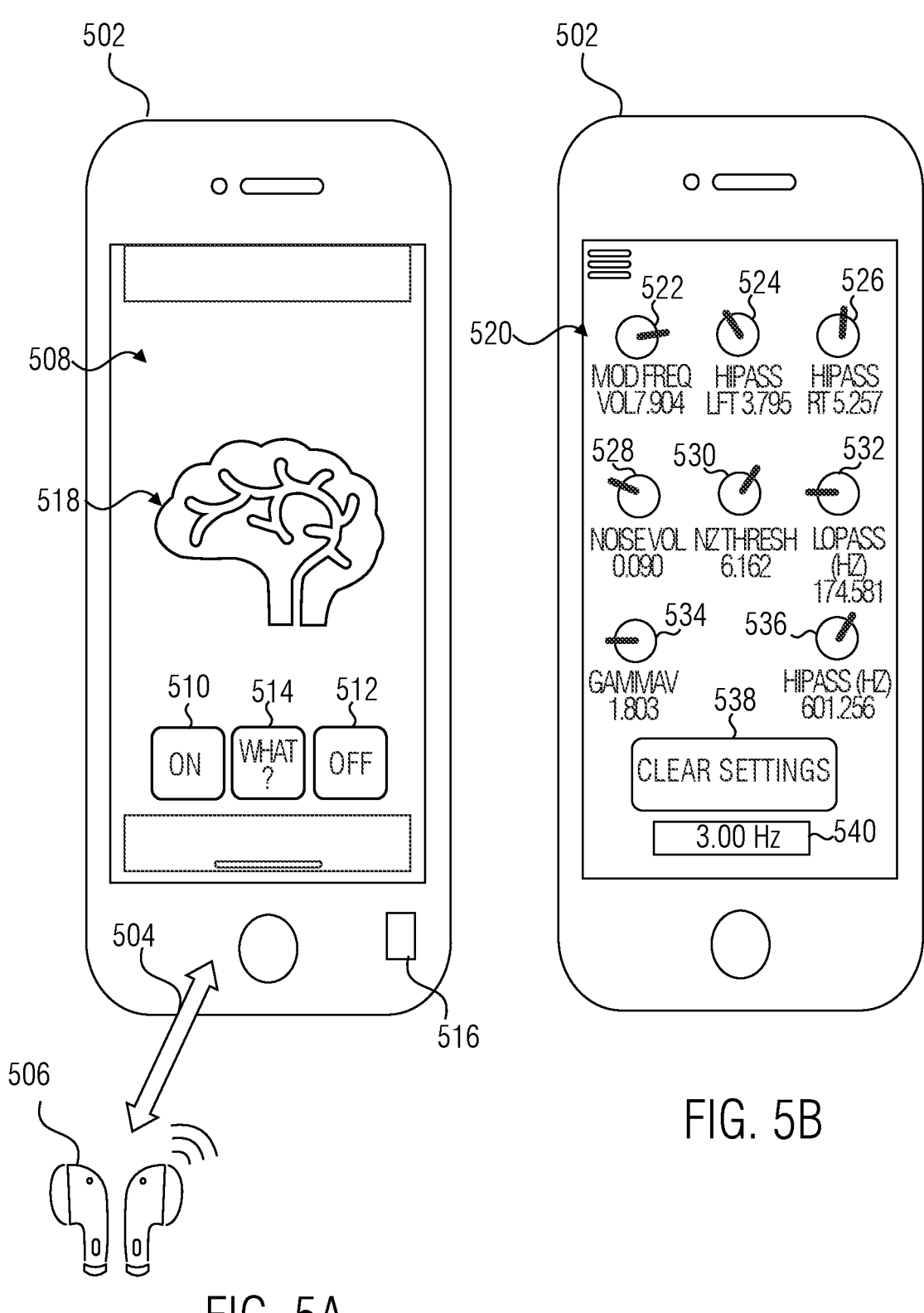
FIG. 5A illustrates generally a first example of an interface for a system or device that can provide auditory stimulation to a user.
FIG. 5B illustrates generally a first example of an interface for a system or device that can provide auditory stimulation to a user.

FIG. 5A and FIG. 5B illustrate generally examples of an interface for a system or device that can provide auditory stimulation to a user. The examples include a mobile device 502, such as can include a mobile phone, tablet computer, or other mobile processing device configured to receive a user input, an audio input, and in response provide an amplitude-modulated output signal. In an example, the mobile device 502 comprises a particular example of the machine 800 discussed elsewhere herein.

The example of FIG. 5A includes the mobile device 502 in communication with headphones 506 using a headphone communication link 504, such as can include a wired or wireless link. The headphones 506 can be used to receive an auditory stimulation signal from the mobile device 502 for delivery to one or more ears of a user. In an example, the mobile device 502 can include an accelerometer 516, such as corresponding to the accelerometer 246 from the interrupt circuit 244 of FIG. 2.

The example of FIG. 5A illustrates generally a home interface 508, such as can be provided on a display of the mobile device 502. The home interface 508 can include various controls, icons, or images. For example, the home interface 508 can include an on button 510 and an off button 512 configured to control operation of an auditory stimulation program. The home interface 508 can include a "WHAT" button 514 that can be used to selectively (e.g., temporarily, or in response to a user input) disengage one or more features of the auditory stimulation system. In an example, in response to user actuation of the "WHAT" button 514, the interrupt circuit 244 can generate the interrupt instruction. The home interface 508 can further include a modulation visualization icon 518, such as can include a pictorial representation of operation of the system. For example, a portion of the modulation visualization icon 518 can change or flash in correspondence with a modulation frequency of an auditory stimulation signal provided by the system.

The example of FIG. 5B illustrates generally a modulation settings interface 520, such as can be provided on the display of the mobile device 502. The modulation settings interface 520 can include various inputs to receive a user input (e.g., from a user, a clinician, a caregiver, etc.) to set or define one or more aspects of an auditory stimulation signal to be provided by the system, such as using the headphones 506.

In the example of FIG. 5B, the inputs comprise graphical dials, such as can represent various relative or absolute settings. The example includes a modulation depth input 522 configured to set or adjust a modulated frequency volume of the auditory stimulation signal. The example includes a first high pass channel amplitude input 524 and a second high pass channel amplitude input 526 configured to set or adjust respective amplitude characteristics of high frequency information in the auditory stimulation signal. The example includes a noise signal amplitude input 528 configured to set or adjust a volume of a noise signal, such as when a noise signal comprises some or all of the auditory stimulation signal. The example includes an ambient signal threshold input 530 that can be used to set or adjust an ambient sound pressure level threshold used by the threshold detector 240. The example includes a low pass frequency input 532 configured to set or adjust a low-pass frequency cutoff such as can be used by the low-pass filter 218. The example includes a gamma signal amplitude input 534 that can be used to set, adjust, or toggle a Gamma wave signal (e.g., additionally or alternatively to other modulation signals). The example includes a high pass frequency input 536 configured to set or adjust a high-pass frequency cutoff such as can be used by the high-pass filter 232. The example further includes a modulation frequency input 540 configured to receive information from a user about a desired modulation frequency of the auditory stimulation signal.

The example of the modulation settings interface 520 further includes a clear settings button 538 to re-set or clear the inputs, or to set one or more of the inputs to predefined or specified values.

FIG. 6 illustrates generally an example of a first method 600 that can be used to provide an auditory stimulation signal to a user. The example can include, at block 602, receiving ambient acoustic information in proximity of the user. Block 602 can include using a microphone or the second audio input 202, to receive the acoustic information.

At block 604, the first method 600 can include amplitude-modulating a low-frequency portion of the ambient acoustic information received at block 602, in an example, block 604 can include using the first processor circuit 210 to generate a low-passed signal and to modulate the low-passed signal to provide a primary modulated output signal.

At block 606, the first method 600 can include combining the primary modulated output signal from block 604 with high frequency information from the ambient acoustic information received at block 602. That is, block 606 can include generating a high-passed signal from the acoustic information received at block 602, such as using the second processor circuit 230, and mixing the high-passed signal with the primary modulated output signal from block 604, such as using the mixer circuit 252.

The first method 600 can further include, at block 608, providing the auditory stimulation signal to a user. In an example, block 608 can include using the headphones 506 to provide the auditory stimulation signal to the user.

Figure 7:
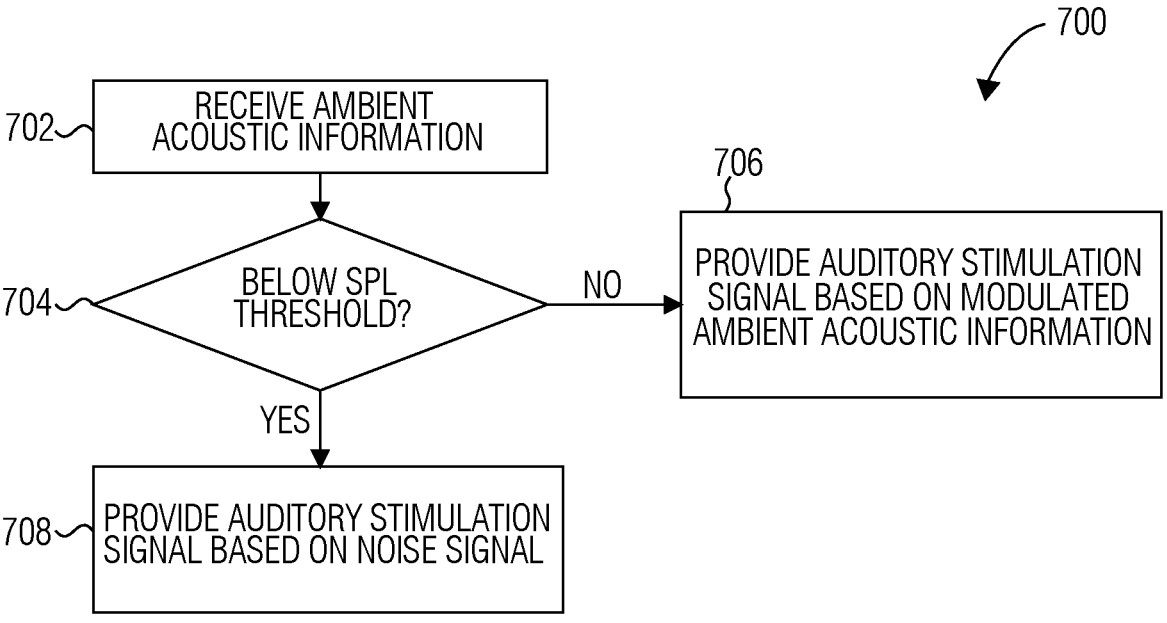
FIG. 7 illustrates generally an example of a second method that can be used to provide an auditory stimulation signal to a user.

FIG. 7 illustrates generally an example of a second method 700 that can be used to provide an auditory stimulation signal to a user. The example can include, at block 702, receiving ambient acoustic information in proximity of a user. In an example, block 702 can include using a microphone or the second audio input 202 from the example of FIG. 2.

At decision block 704, the second method 700 can include determining whether the acoustic information received at block 702 meets a threshold sound pressure level (SPL) condition. If the acoustic information is not below the SPL threshold, then the second method 700 can continue at block 706. At block 706, the second method 700 can include providing an auditory stimulation signal based on modulated ambient acoustic information. For example, block 706 can include or use the first method 600 to provide an auditory stimulation signal based on a combination of high-passed and modulated low-passed information from the acoustic signal.

If the acoustic information is below the SPL threshold at decision block 704, then the second method 700 can continue at block 708. At block 708, the second method 700 can include providing an auditory stimulation signal based on a noise signal. That is, block 708 can include providing an amplitude-modulated noise signal as all or a portion of an auditor stimulation signal for the user.

Figure 8:
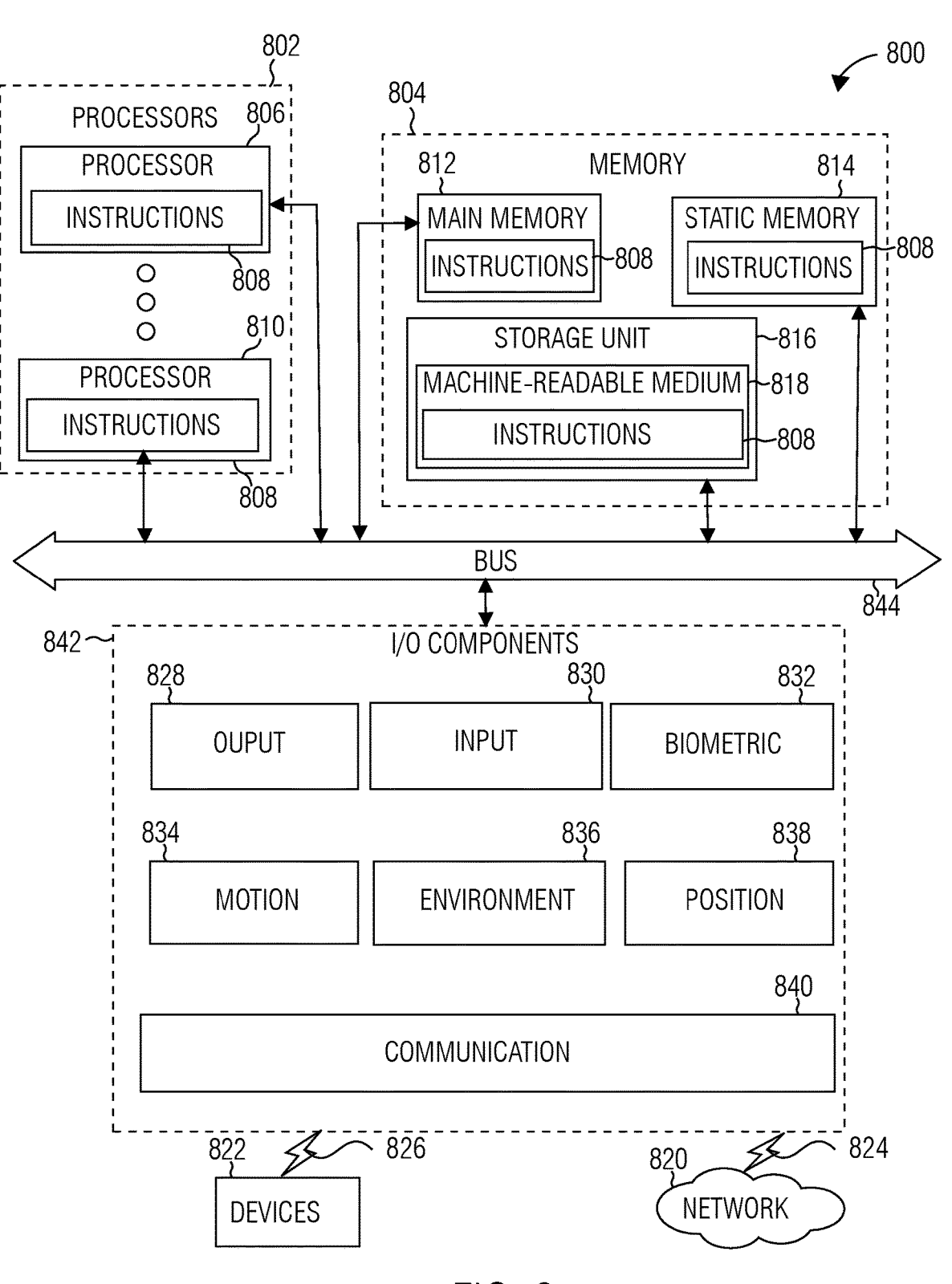
FIG. 8 is a diagrammatic representation of a machine in the form of a computer system within which a set of instructions may be executed for causing the machine to perform any one or more of the methodologies discussed herein, according to an example embodiment.

FIG. 8 is a diagrammatic representation of a machine 800 within which instructions 808 (e.g., software, a program, an application, an applet, an app, or other executable code) for causing the machine 800 to perform any one or more of the methodologies discussed herein may be executed. For example, the instructions 808 may cause the machine 800 to execute any one or more of the methods described herein, such as can include various audio signal processing methods or algorithms, such as can be used to prepare or provide an auditory stimulation signal to a user. The instructions 808 transform the general, non-programmed machine 800 into a particular machine 800 programmed to carry out the described and illustrated functions in the manner described. The machine 800 may operate as a standalone device or may be coupled (e.g., networked) to other machines. In a networked deployment, the machine 800 may operate in the capacity of a server machine or a client machine in a server-client network environment, or as a peer machine in a peer-to-peer (or distributed) network environment. The machine 800 may comprise, but not be limited to, a server computer, a client computer, a personal computer (PC), a tablet computer, a laptop computer, a netbook, a set-top box (STB), a PDA, an entertainment media system, a cellular telephone, a smart phone, a mobile device, a wearable device (e.g., a smart watch), a smart home device (e.g., a smart appliance), other smart devices, a web appliance, a network router, a network switch, a network bridge, or any machine capable of executing the instructions 808, sequentially or otherwise, that specify actions to be taken by the machine 800. Further, while only a single machine 800 is illustrated, the term "machine" shall also be taken to include a collection of machines that individually or jointly execute the instructions 808 to perform any one or more of the methodologies discussed herein.

The machine 800 may include processors 802, memory 804, and I/O components 842, which may be configured to communicate with each other via a bus 844. In an example embodiment, the processors 802 (e.g., a Central Processing Unit (CPU), a Reduced Instruction Set Computing (RISC) processor, a Complex Instruction Set Computing (CISC) processor, a Graphics Processing Unit (GPU), a Digital Signal Processor (DSP), an ASIC, a Radio-Frequency Integrated Circuit (RFIC), another processor, or any suitable combination thereof) may include, for example, a processor 806 and a processor 810 that execute the instructions 808. The term "processor" is intended to include multi-core processors that may comprise two or more independent processors (sometimes referred to as "cores") that may execute instructions contemporaneously. Although FIG. 8 shows multiple processors 802, the machine 800 may include a single processor with a single core, a single processor with multiple cores (e.g., a multi-core processor), multiple processors with a single core, multiple processors with multiples cores, or any combination thereof.

The memory 804 can include a main memory 812, a static memory 814, and a storage unit 816, accessible to the processors 802 via the bus 844. The main memory 804, the static memory 814, and storage unit 816 store the instructions 808 embodying any one or more of the methodologies or functions described herein. The instructions 808 may also reside, completely or partially, within the main memory 812, within the static memory 814, within a machine-readable medium 818 within the storage unit 816, within at least one of the processors 802 (e.g., within the processor's cache memory), or any suitable combination thereof, during execution thereof by the machine 800.

The I/O components 842 may include a wide variety of components to receive input, provide output, produce output, transmit information, exchange information, capture measurements, and so on. The specific I/O components 842 that are included in a particular machine will depend on the type of machine. For example, portable machines such as mobile phones may include a touch input device or other such input mechanisms (e.g., corresponding to the modulation settings interface 520), while a headless server machine will likely not include such a touch input device. It will be appreciated that the I/O components 842 may include many other components that are not shown in FIG. 8, In various example embodiments, the I/O components 842 may include output components 828 and input components 830. The output components 828 may include visual components (e.g., a display such as a plasma display panel (PDP), a light emitting diode (LED) display, a liquid crystal display (LCD), a projector, or a cathode ray tube (CRT)), acoustic components (e.g., speakers, the headphones 506, etc.), haptic components (e.g., a vibratory motor, resistance mechanisms), other signal generators, and so forth. The input components 830 may include alphanumeric input components (e.g., a keyboard, a touch screen configured to receive alphanumeric input, a photo-optical keyboard, or other alphanumeric input components), point-based input components e.g., a mouse, a touchpad, a trackball, a joystick, a motion sensor, or another pointing instrument), tactile input components (e.g., a physical button, a touch screen that provides location and/or force of touches or touch gestures, or other tactile input components), audio input components (e.g., a microphone), and the like.

In further example embodiments, the I/O components 842 may include biometric components 832, motion components 834, environmental components 836, or position components 838, among a wide array of other components. For example, the biometric components 832 include components to detect expressions (e.g., hand expressions, facial expressions, vocal expressions, body gestures, or eye tracking), measure biosignals (e.g., blood pressure, heart rate, body temperature, perspiration, or brainwaves), identify a person (e.g., voice identification, retinal identification, facial identification, fingerprint identification, or electroencephalogram-based identification), and the like. The motion components 834 include acceleration sensor components (e.g., the accelerometer 246), gravitation sensor components, rotation sensor components (e.g., gyroscope), and so forth. The environmental components 836 include, for example, illumination sensor components (e.g., photometer), temperature sensor components (e.g., one or more thermometers that detect ambient temperature), humidity sensor components, pressure sensor components (e.g., barometer), acoustic sensor components (e.g., one or more microphones that detect background noise), proximity sensor components (e.g., infrared sensors that detect nearby objects), gas sensors (e.g., gas detection sensors to detection concentrations of hazardous gases for safety or to measure pollutants in the atmosphere), or other components that may provide indications, measurements, or signals corresponding to a surrounding physical environment of the user. Information from any one or more of the motion components 834 or the environmental components 836 or other sensors or devices can similarly be used to update or change a modulation parameter or setting of a system that provides auditory stimulation. The position components 838 include location sensor components (e.g., a GPS receiver component), altitude sensor components (e.g., altimeters or barometers that detect air pressure from which altitude may be derived), orientation sensor components (e.g., magnetometers), and the like.

Communication may be implemented using a wide variety of technologies. The I/O components 842 further include communication components 840 operable to couple the machine 800 to a network 820 or devices 822 via a coupling 824 and a coupling 826, respectively. For example, the communication components 840 may include a network interface component or another suitable device to interface with the network 820. In further examples, the communication components 840 may include wired communication components, wireless communication components, cellular communication components, Near Field Communication (NFC) components, Bluetooth® components (e.g., Bluetooth® Low Energy), Wi-Fi® components, and other communication components to provide communication via other modalities. The devices 822 may be another machine or any of a wide variety of peripheral devices (e.g., a peripheral device coupled via a USB).

The various memories (e.g., memory 804, main memory 812, static memory 814, and/or memory of the processors 802) and/or storage unit 816 may store one or more sets of instructions and data structures (e.g., software) embodying or used by any one or more of the methodologies or functions described herein. These instructions (e.g., the instructions 808), when executed by processors 802, cause various operations to implement the disclosed embodiments.

The instructions 808 may be transmitted or received over the network 820, using a transmission medium, via a network interface device (e.g., a network interface component included in the communication components 840) and using any one of a number of well-known transfer protocols (e.g., hypertext transfer protocol (HTTP)). Similarly, the instructions 808 may be transmitted or received using a transmission medium via the coupling 826 (e.g., a peer-to-peer coupling) to the devices 822.

The solutions discussed herein can be used to treat or improve symptoms of a variety of disorders and conditions including but not limited to dementias (including Alzheimer's Dementia), Parkinson's Disease, Chronic Traumatic Encephalopathy, anxiety, and ADHD, such as using different parameters or settings for each condition and/or for each user. The solutions discussed herein can be added to the functionality of a variety of existing hearing aids or assisted listening device, such as in combination with sound processing for improved audition. The injection of noise, or use of modulated noise, can be provided in any device with headphones or other hearing devices such as for people with tinnitus. In an example, the solution can be included in or implemented using a smartphone app such as can be used with a smartphone and pair of earbuds or other headphones. In an example, the solution can include a clinical version for use in hospitals such as with a set of headphones with built-in processing or an external processing unit. Such a device can amplitude-modulate the intense sounds in a hospital environment to either prevent hospital delirium from developing (a pervasive problem with hospitalized elderly) or to help calm anxious patients.

In an example, the auditory stimulation systems and methods discussed herein can be used together with EEG activity configured to sense electrical activity of a brain. The auditory stimulation can be triggered or adjusted, for example, depending on measured brain activity. In an example, the EEG can be configured to detect an impending seizure and, in response, the auditory stimulation device can attempt to prevent or disrupt the seizure by stimulating the brain with an alternative signal.

The above description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples one or more aspects thereof) shown or described herein.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

What is claimed is:

1. A system for inducing brainwave activity using auditory stimulation, the system comprising:

an audio input configured to receive ambient acoustic information from an environment of a user;

a modulation reference signal generator configured to generate a modulation reference signal based on a modulation input;

a noise signal generator configured to generate a noise signal;

a first audio band processor circuit configured to provide a primary modulated output signal based on a first frequency portion of the ambient acoustic information and on the modulation reference signal, and to provide a secondary modulated output signal based on the noise signal and on the modulation reference signal; and a mixer circuit configured to provide an auditory stimulation signal, wherein when the ambient acoustic information indicates an ambient sound pressure level (SPL) meets or exceeds a specified threshold SPL, the auditory stimulation signal includes the primary modulated output signal from the first audio band processor circuit and a different second frequency portion of the ambient acoustic information, and when the ambient acoustic information indicates the ambient SPL is less than the specified threshold SPL, the auditory stimulation signal includes the secondary modulated output signal.

2. The system of claim 1, wherein the first audio band processor circuit is configured to provide the primary modulated output signal based on a relatively lower frequency portion of the ambient acoustic information, and wherein the different second frequency portion includes a relatively higher frequency portion of the ambient acoustic information.

3. The system of claim 1, wherein the first audio band processor circuit is configured to provide the primary modulated output signal based on a relatively higher frequency portion of the ambient acoustic information, and wherein the different second frequency portion includes a relatively lower frequency portion of the ambient acoustic information.

4. The system of claim 1, wherein the different second frequency portion of the ambient acoustic information corresponds to a first frequency band that comprises human speech intelligibility information, and wherein the first frequency portion of the ambient acoustic information corresponds to acoustic information that is outside of the first frequency band.

5. The system of claim 1, wherein the first audio band processor circuit is configured to amplitude modulate the first frequency portion of the ambient acoustic information according to the modulation reference signal to provide the primary modulated output signal.

6. The system of claim 1, further comprising a second audio band processor circuit configured to apply a gain adjustment and a high pass filter to the ambient acoustic information to provide the different second frequency portion to the mixer circuit.

7. The system of claim 6, wherein the second audio band processor circuit is configured to augment, in the different second frequency portion, one or more frequencies or frequency bands associated with intelligibility of human speech.

8. The system of claim 1, wherein the first audio band processor circuit comprises a random number generator configured to generate an amplitude control signal, and wherein an amplitude of the primary modulated output signal depends in part on a value of the amplitude control signal.

9. The system of claim 1, wherein the modulation reference signal generator is configured to generate the modulation reference signal with a frequency drift, wherein the modulation input indicates a modulation reference frequency and a modulation drift magnitude.

10. The system of claim 1, further comprising an ancillary reference signal generator configured to generate an ancillary reference signal based on the modulation input;

wherein the first audio band processor circuit is configured to provide a further modulated output signal based on the primary modulated output signal and the ancillary reference signal; and wherein the mixer circuit is configured to provide the auditory stimulation signal using the further modulated output signal and the different second frequency portion of the ambient acoustic information.

11. The system of claim 1, further comprising an accelerometer configured to generate an interrupt instruction, wherein when the interrupt instruction is asserted, the mixer circuit is configured to change a magnitude relationship of the primary modulated output signal and the different second frequency portion of the ambient acoustic information in the auditory stimulation signal.

12. The system of claim 1, wherein in response to an interrupt instruction that is based on an accelerometer output signal, the mixer circuit is configured to interrupt the auditory stimulation signal and provide an augmented version of the ambient acoustic information to the user.

13. The system of claim 1, further comprising a mobile device with a microphone and a user interface;

wherein the audio input comprises the microphone of the mobile device; and wherein the user interface comprises the modulation input, and the modulation input includes instructions for a modulation frequency or a modulation amplitude for the primary modulated output signal.

14. The system of claim 1, further comprising an in-ear assisted listening device configured to provide the auditory stimulation signal to the user.

\* \* \* \* \*